(12) United States Patent
Yazicioglu

(10) Patent No.: US 8,755,868 B2
(45) Date of Patent: Jun. 17, 2014

(54) ADAPTIVE SAMPLING

(75) Inventor: Refet Firat Yazicioglu, Leuven (BE)

(73) Assignee: IMEC, Leuven (BE)

( * ) Notice: Subject to any disclaimer, the term of this patent is extended or adjusted under 35 U.S.C. 154(b) by 801 days.

(21) Appl. No.: 12/882,118

(22) Filed: Sep. 14, 2010

(65) Prior Publication Data

US 2011/0066053 A1 Mar. 17, 2011

Related U.S. Application Data

(60) Provisional application No. 61/242,299, filed on Sep. 14, 2009, provisional application No. 61/365,296, filed on Jul. 16, 2010.

(51) Int. Cl.
*A61B 5/04* (2006.01)

(52) U.S. Cl.
USPC .......................................................... 600/509

(58) Field of Classification Search
USPC ................ 600/509, 521; 341/123; 700/73–73
See application file for complete search history.

(56) References Cited

U.S. PATENT DOCUMENTS

| | | | |
|---|---|---|---|
| 729,168 A | 5/1903 | Henderson | |
| 3,667,056 A | 5/1972 | Allington et al. | |
| 4,610,254 A | 9/1986 | Morgan et al. | |
| 4,669,301 A | 6/1987 | Kratt et al. | |
| 5,020,541 A | 6/1991 | Marriott | |
| 5,197,479 A | 3/1993 | Hubelbank et al. | |
| 5,263,486 A * | 11/1993 | Jeffreys | 600/508 |
| 5,381,803 A | 1/1995 | Herleikson et al. | |
| 6,714,813 B2 | 3/2004 | Ishigooka et al. | |
| 6,812,254 B1 | 11/2004 | Weil et al. | |
| 8,068,905 B2 | 11/2011 | Freeman et al. | |
| 2003/0006782 A1 | 1/2003 | Shambroom et al. | |
| 2007/0060802 A1 | 3/2007 | Ghevondian et al. | |
| 2008/0183098 A1 | 7/2008 | Denison et al. | |
| 2010/0324404 A1 | 12/2010 | Harrold et al. | |
| 2011/0092834 A1 * | 4/2011 | Yazicioglu et al. | 600/509 |

FOREIGN PATENT DOCUMENTS

| | | |
|---|---|---|
| EP | 0540144 | 5/1993 |
| EP | 0884851 | 12/1998 |
| EP | 1754441 A1 | 2/2007 |
| EP | 2086111 | 8/2009 |
| WO | WO 2004/052198 A1 | 6/2004 |
| WO | WO 2008/073528 A1 | 6/2008 |

OTHER PUBLICATIONS

R.F. Yazicioglu et al., "Ultra-Low-Power Wearable Biopotential Sensor Nodes",.31[st] Annual International Conference of the IEEE EMBS Minneapolis, Minnesota, USA, pp. 3205-3208, Sep. 2-6, 2009.

(Continued)

*Primary Examiner* — Mark W Bockelman
(74) *Attorney, Agent, or Firm* — Knobbe Martens Olson & Bear LLP

(57) ABSTRACT

A method and apparatus is disclosed for adaptively sampling an analogue signal to increase the sampling rate in the presence of high frequency content within the signal, for example, QRS complex of an ECG signal. In one aspect, a change in a derivative of the analogue signal is used to control a voltage-controlled oscillator to provide a clock signal for an analogue-to-digital converter. The change in the derivative is compared to an automatically controlled threshold value. The clock signal controls the sampling rate of the analogue-to-digital converter so that the sampling rate is increased from one level, where only P and T waves are present to another higher level when the QRS complex has been detected.

16 Claims, 14 Drawing Sheets

Convolution of Adaptively Sampled ECG and Wavelet

(56) References Cited

OTHER PUBLICATIONS

R.F. Yazicioglu et al., "A 200 μW Eight-Channel EEG Acquisition ASIC for Ambulatory EEG Systems", IEEE Journal of Solid-State Circuits, vol. 43, No. 12, pp. 3025-3038, Dec. 2008.
A.-T. Avestruz et al,. "A 5 μW/Channel Spectral Analysis IC for Chronic Bidirectional Brain-Machine Interfaces", IEEE Journal of Solid-State Circuits, vol. 43, No. 12, pp. 3006-3024, Dec. 2008.
C.C. Enz et al., "Circuit Techniques for Reducing the Effects of Opamp Imperfections", Proc. of IEEE, vol. 84, No. 11, pp. 1584-1614, Nov. 1996.
R.R. Harrison et al., "A Low-Power Low-Noise Cmos Amplifier for Neural Recording Applications", IEEE J. Solid State Circuits, vol. 38, No. 6, pp. 958-965, Jun. 2003.
J. Ottenbacher et al., "Reliable Motion Artifact Detection for ECG Monitoring Systems with Dry Electrodes", IEEE EMBS Conf., pp. 1695-1698, Aug. 2008.
X.D. Zou et al., "A 1V 450nW Fully Integrated Programmable Biomedical Sensor Interface System", IEEE J. of Solid-State Circuits, vol. 44, No. 4, pp. 1067-1077, Apr. 2009.
ANSI/AAMI-EC13, "American national standards for cardiac monitors, hearth rate meters and alarms", Association for the Advancement of Medical Instrumentation, 2002.
B. Gyselinckx et al., "Human++: Energing Technology for Body Area Networks", Very Large Scale Integration, 2006 IFIP International Conference, pp. 175-180, Oct. 2006.
J. Penders et al., "Human++: from Technology to Emerging Health Monitorning Concepts", Proceedings of the 5th International Workshop on Wearable and Implantable Body Sensor Networks, pp. 94-98, 1st to 3rd Jun. 2008.
R.F. Yazicioglu et al., "A 60μW 60nV/√Hz Readout Front-end for Portable Biopotential Acquisition Systems", IEEE J. Solid-State Circuits, vol. 42, No. 5, pp. 110-1110, May 2007.
C Enz., "A CMOS Chopper Amplifier", IEEE J. Solid-State Circuits, vol. 22, No. 3, pp. 335-342, Jun. 1987.
MSJ Steyaert et al., "A Micropower Low-Noise Monolithic Instrumentation Amplifier for Medical Purposes", IEEE J. Solid-State Circuits, vol. sc-22, No. 6, lines 1163 to 1168, Dec. 1987.
I Romero et al., "Low-Power Robust Beat Detection in Ambulatory Cardiac Monitoring", IEEE BioCAS, pp. 249-252, Nov. 2009.
H. Tam et al., "Minimizing Electrode Motion Artifact by Skin Abrasion", IEEE Trans. on Biomedical Engineering, vol. BME-24, pp. 134-139, 1977.
M Trakimas et al., "A 0.8V Asynchronous ADC for Energy Constrained Sensing Application", IEEE CICC, pp. 173-176, Sep. 2008.
Jalaleddine et al., "ECG data compression techniques—A unified approach", IEEE trans on Biomed. Eng., vol. 37, No. 4, Apr. 1990.
Kalinin et al., "A simple method to adapt time sampling of the analog signal", Nuclear Instruments and Methods in Physics Research A 524 (2004), pp. 374-376.
H. Kim et al., "A Low Cost Quadratic Level ECG Compression Algorithm and Its Hardware Optimization for Body Sensor Network System", IEEE EMBS 2008, pp. 5490-5493, Aug. 2008.
Extended European Search Report for European Patent Application No. 10176687.1-1265 dated Nov. 21, 2011.
Bohs L N et al., "Real-time adaptive sampling with the fan algorithm", Medical and Biological Engineering and Computing, Springer, Heildelberg, DE, vol. 26, No. 6, Nov. 1, 1988, pp. 563-573.
Barr et al., "Adaptive sampling of cardiac waveforms", Journal of Electrocardiology, Elsevier Science, vol. 21, Jan. 1, 1988, pp. S57-S60.
Rieger R et al., "An Adaptive Sampling System for Sensor Nodes in Body Area Networks", IEEE Transactions of Neural Systems and Rehabilitation Engineering, IEEE Service Center, New York, NY, US, vol. 17, No. 2, Apr. 1, 2009, pp. 183-189.
Bohs L N et al., "Prototype for real-time adaptive sampling using the fan algorithm" , Medical and Biological Engineering and Computing, Springer, Heildelberg, DE, vol. 26, No. 6, Nov. 1, 1988, pp. 574-583.
Rieger R. et al., "A Signal Based Clocking Scheme for A/D Converters in Body Sensor Networks", Tencon 2006. 2006 IEEE Region 10 Conference, IEEE, PI, Nov. 14, 2006, pp. 1-4.
Extended European search report for European Patent Application No. 10176639.2-1265 dated Dec. 23, 2010 by European Patent Office.
US Office Action for U.S. Appl. No. 12/882,126 mailed Jul. 3, 2012 by the U.S. Patent and Trademark Office.

* cited by examiner

ADAPTIVE SAMPLING

CROSS REFERENCE TO RELATED APPLICATIONS

This application claims priority under 35 U.S.C. §119(e) to U.S. provisional patent application 61/242,299 filed on Sep. 14, 2009 and U.S. provisional patent application 61/365,296 filed on Jul. 16, 2010. This application is related to U.S. application Ser. No. 12/882,126, filed on the same day herewith and issued as U.S. Pat. No. 8,454,505 on Jun. 4, 2013, and titled "METHOD AND ELECTRONIC MEDICAL DEVICE FOR SIMULTANEOUSLY MEASURING AN IMPEDANCE AND A BIOPOTENTIAL SIGNAL," and U.S. application Ser. No. 12/882,120, filed on the same day herewith and titled "ANALOGUE SIGNAL PROCESSORS." Each of the above applications is hereby incorporated by reference in its entirety.

BACKGROUND OF THE INVENTION

1. Field of the Invention

The present disclosure relates to adaptive sampling and is more particularly, although not exclusively concerned with the adaptive sampling of biopotential signals.

2. Description of the Related Technology

Power efficiency of readout circuits for ambulatory monitoring of biopotential signals has been significantly improved during recent years, leaving digital signal processing and wireless transmission dominating the system power. One of the key problems of the current wireless biomedical systems is the vast amount of data that needs to be processed by a digital signal processor (DSP) and/or that needs to be transmitted over the wireless link. Such a vast amount of data considerably limits the power autonomy of these systems. Therefore, the compression of data is gaining more attention for reducing the amount of processing and the data transmitted over the wireless link.

The sampling rate of biopotential signals and, more in particular, those of ECG signals, is conventionally selected according to the bandwidth of the signal, which is defined by the QRS complex part of the ECG trace In addition, some diagnostic tools such as heart rate variability (HRV) analysis, may require even higher sampling rate due to the required time resolution to precisely find the R point in the QRS complex. However, such high and constant sampling rate over the entire ECG signal significantly increases the data rate and leads to increasing power dissipation.

Commonly portable biopotential monitoring systems follow one of two approaches:
1. The signals are processed in the system and the results are transmitted; or
2. The signals are continuously streamed and the processing takes place at the receiver side.

The first type of system can make use of data compression to reduce DSP work load. The second type of system can benefit from data compression by transmitting significantly less data.

SUMMARY OF CERTAIN INVENTIVE ASPECT

In accordance with a first aspect of the present disclosure, there is provided a method for adaptively sampling an analogue signal, the method comprising the steps of: a) determining a derivative of the analogue signal; b) detecting a change in the derivative of the analogue signal; c) sampling the analogue signal using a sampling frequency; and d) using the change in the derivative of the analogue signal to control the sampling frequency of the analogue signal; wherein step d) comprises comparing the change in the derivative of the analogue signal with an automatically controlled threshold value.

Step d) comprises generating the automatically controlled threshold value from an expected average activity value and an extracted average activity value. In addition, step d) may further comprise comparing the extracted average activity value with the expected average activity value.

The term "average activity value" refers to the average activity of the analogue signal. In particular, this refers to the average heart or beat rate of an ECG signal that forms the analogue signal. Consequently, the term "extracted average activity value" refers to the an actual activity value extracted from the analogue signal and the term "expected average activity value" refers to an expected activity value that is determined as what should be expected from the analogue signal.

Advantageously, step d) further includes the step of deriving the extracted average activity value from the analogue signal.

The analogue signal may comprise an electrocardiogram signal and step d) therefore comprises deriving the expected average activity value from a beat rate of the electrocardiogram signal.

Ideally, step c) comprises adjusting the sampling frequency to sample the analogue signal in accordance with the comparison between the derivative of the analogue signal and the threshold value.

In accordance with another aspect of the present disclosure, there is provided adaptive sampling apparatus for adaptively sampling an analogue signal, the sampling apparatus comprising: a sampling device for sampling the analogue signal at a sampling frequency; and a control device for controlling the sampling device; wherein the control device comprises an activity detection device that determines a derivative of the analogue signal and uses the derivative of the analogue signal to alter the sampling frequency of the sampling device; and in that the activity detector further comprises a comparator that compares the derivative of the analogue signal with an automatically controlled variable threshold value.

It is preferred that the automatically controlled threshold value is generated from an expected average activity value and an extracted average activity value.

The comparator is used to generate a difference between the extracted activity value and the expected average activity value that is used to automatically control the threshold value. Ideally, the threshold value is increased when the extracted average activity value is greater than the expected average activity value and is decreased when the extracted average activity value is less than the expected average activity value.

The activity detection device comprises a differentiator that generates the derivative of the analogue signal. A sampling frequency selector may also be provided that uses the derivative of the analogue signal to select the sampling frequency of the sampling device.

In one embodiment, the sampling device comprises an analogue-to-digital converter that converts the analogue signal into a digital representation thereof in accordance with the sampling frequency.

Another inventive aspect relates to a method and a system for adaptive sampling an analogue signal. The system comprises a conversion block arranged for converting an analogue input signal into a digital representation of the analogue signal at a predetermined sampling frequency. The system further comprises a control block arranged for setting the predetermined sampling frequency. The control block comprises an activity detection block arranged for detecting the rate of change in or the derivative of the analogue input signal. The activity detection block comprises a differentiator arranged for generating the derivative of the analogue input signal and a comparator device arranged for comparing the derivative to an automatically derived and controlled threshold value thereby outputting a quantized representation or level of the rate of change of the analogue signal.

Dependent on the outcome of the comparison, a sampling frequency is selected (to each quantization level, a sampling rate is assigned) or adjusted (by means of a voltage controlled oscillator which is controlled by the outcome of the comparison). The analogue input signal is sampled with an adaptive sampling rate depending on the rate of change of the input signal. If a significant change is determined (above threshold), the sampling frequency is adapted. The rate of change is monitored by the differentiator and compared to an automatically derived and controlled variable threshold. In other words, the steepness of the slope of the analogue input signal is monitored. The sampling rate is adapted continuously and immediately in relation to the result of the activity detection block.

The control block comprises a threshold generator for setting a given threshold value. In an embodiment, the given threshold value is a fixed, predetermined value based on signal characteristics of the analogue input signal. In an embodiment, the given threshold value is continuously updated by means of a feedback loop wherein the outcome of the comparison and the signal characteristics of the analogue input are combined and taken into account.

The sampling rate is adapted according to the rate of change of the input signal. This enables the sampling of an ECG signal with significantly reduced data rate but without loss of information. In one aspect, the sampling scheme reduces the ADC power dissipation, enables the processing of ECG signals with lower power dissipation, and reduces the power dissipation of the radio while streaming the ECG signals.

Signal compression at the ADC or digital level is the most attractive in terms of trade-off between power dissipation and reducing the information content of the signal. This reduction in the data rate not only reduces the power dissipation of the ADC but also it significantly reduces the power dissipation of the DSP platform as well as the power dissipation of the radio or wireless link. The low power dissipation of the building blocks implementing the adaptive sampling process leads to a smarter ADC with significantly lower power dissipation due to the reduced data rate.

In accordance with a further aspect of the present disclosure, there is provided an analogue signal processor comprising the adaptive sampling apparatus as described above. Ideally, the analogue signal processor is in the form of an application specific integrated circuit.

An analogue signal processor ASIC for ECG signals is described herein. In addition to the power-efficient extraction of ECG signals, an adaptive sampling scheme for data reduction, continuous-time electrode-tissue impedance monitoring for sensing the presence of motion artifacts, and band-power extraction for beat detection is described.

BRIEF DESCRIPTION OF DRAWINGS

For a better understanding of the present disclosure, reference will now be made, by way of example only, to the accompanying drawings in which.

DETAILED DESCRIPTION OF CERTAIN ILLUSTRATIVE EMBODIMENTS

Figure 1:
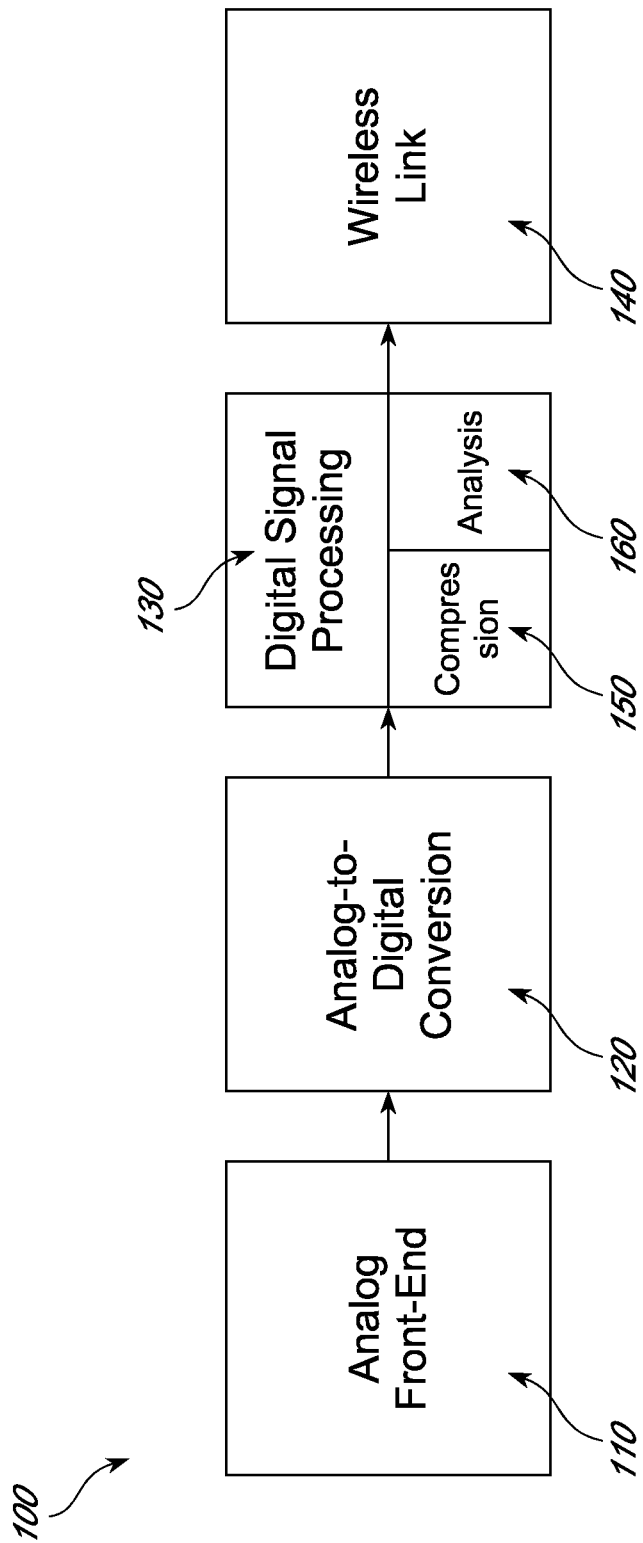
FIG. 1 illustrates a block diagram of a conventional wireless biomedical system.

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes.

Certain embodiments relate to an analogue signal processor ASIC for ECG signals, and others relate to an adaptive sampling scheme for data reduction.

Certain embodiments relate to a method for adaptive sampling of an analogue signal to overcome the problems of the prior art, namely, the adaptive sampling of signals with an automatically controlled variable threshold.

Certain embodiments relate to a system for carrying out the method of adaptive sampling of an analogue signal in accordance with an automatically controlled variable threshold.

Referring initially to FIG. 1, a block diagram of a conventional wireless biomedical system 100 is shown. The system 100 comprises an analogue front-end 110, an analogue-to-digital converter (ADC) 120, a digital signal processor (DSP) 130 and a radio or wireless link 140. The analogue front-end 110 extracts an electrocardiogram (ECG) signal from a subject (not shown) and passes that signal to the DSP 130 where the signal is digitized using a fixed conversion speed. The digitized signal is then passed to the DSP 130 for processing where it can be compressed in a compression module 150 and features extracted in a feature extraction module 160. The output from the DSP 130 is then passed to the radio or wireless link 140 for transmission to a receiver (not shown).

In one embodiment, the benefit of using an adaptive sampling scheme is the reduction of the amount of data for processing before it reaches the DSP stage. This can lead to considerable power saving in the DSP stage. A block diagram of the ADC stage with adaptive sampling rate is illustrated in FIG. 2.

Figure 2:
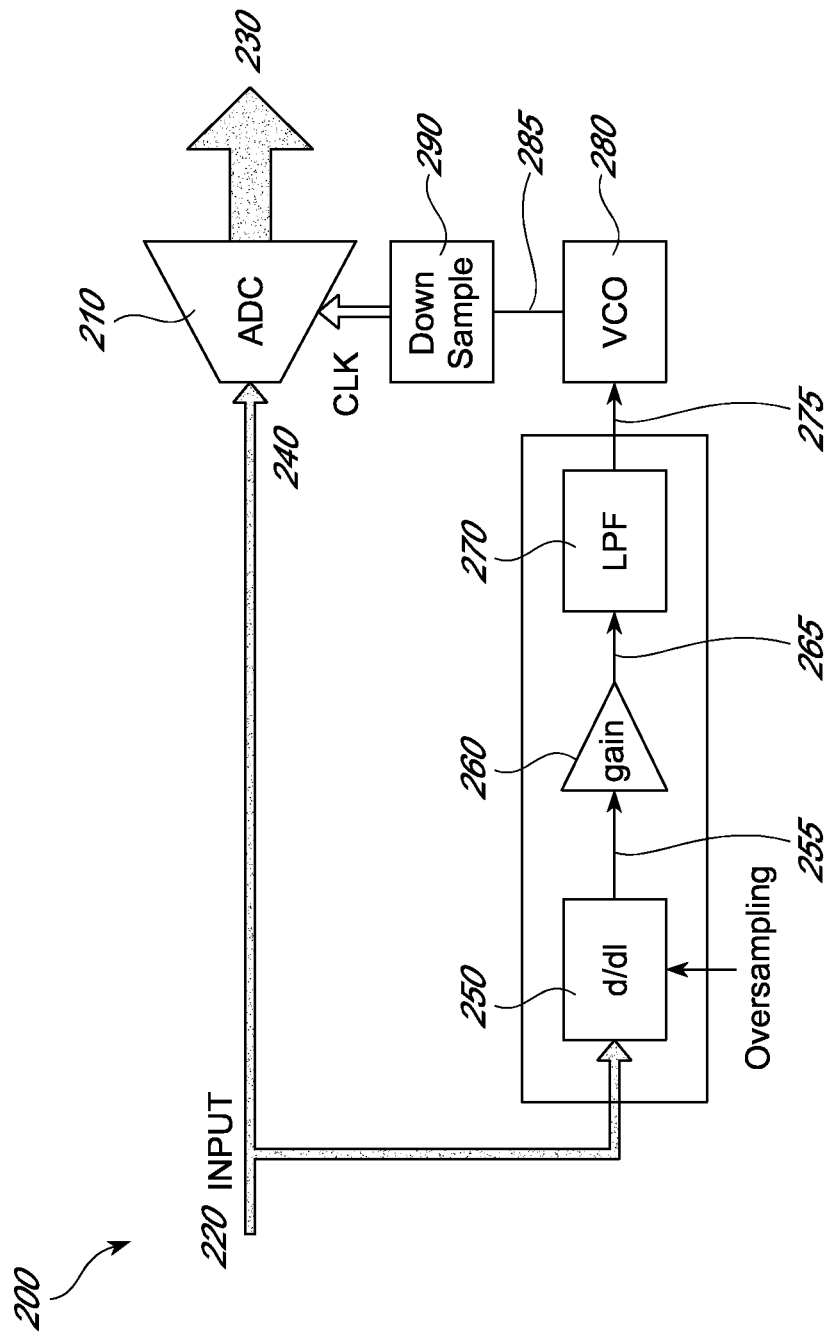
FIG. 2 illustrates a block diagram of the adaptive based sampling system.

In FIG. 2, an adaptive sampling system 200 in accordance with one embodiment is shown. The system 200 comprises an analogue-to-digital converter (ADC) 210 that receives an analogue signal from the analogue front-end 110 (FIG. 1) as its input signal 220. An output signal 230 from the ADC 210 is then passed to the DSP 130 (FIG. 1). A clock signal 240 is supplied to the ADC 210 that is derived from the input signal 220.

For derivation of the clock signal 240, input signal 220 is passed to a slope monitoring circuit 250 that monitors the change in slope of the input signal 220. The slope monitoring circuit 250 over-samples the input signal 220 and calculates its slope. Information about the slope is extracted by taking the derivative of the input signal 220 and output signal 255 from the slope monitoring circuit 250 corresponds to the derivative of the input signal 220. Output signal 255 is passed to an amplifier 260 where it is amplified to provide an amplified derivative signal 265. The amplified derivative signal 265 is filtered in a low-pass filter (LPF) unit 270 to produce an amplified and filtered derivative signal 275. The amplified and filtered derivative signal 275 is used to control the oscillation frequency of a voltage-controlled oscillator (VCO) 280. The output of the VCO 285 is down-sampled in module 290 and adjusts the sampling and/or operating frequency of the ADC 210, the down-sampled signal forming the clock signal 240. On receipt of the clock signal 240, the ADC 210 samples and digitizes input signal 220.

Figure 3:
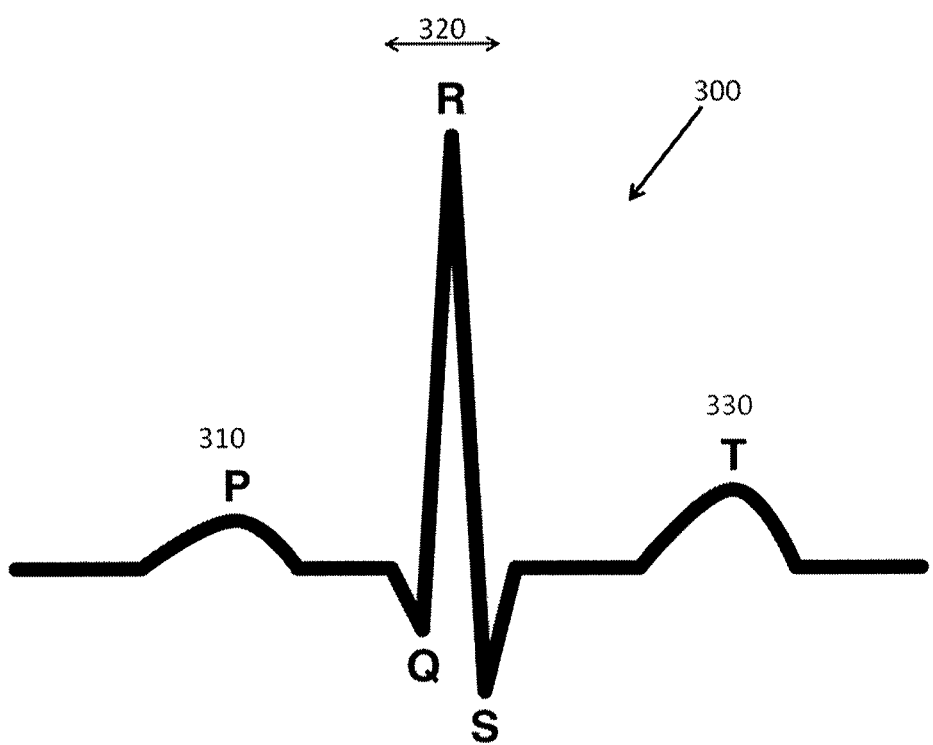
FIG. 3 illustrates a typical ECG signal input to the adaptive based sampling system of FIG. 2.

FIG. 3 illustrates a typical ECG signal 300 that consists of a P wave 310, QRS complex 320 and a T wave 330. Of three of these signals 310, 320, 330, the QRS complex 320 has the highest frequency. Therefore, the sampling rate of the system in one embodiment is selected to achieve high resolution in the QRS complex 320. However, as the QRS complex 320 has a relatively short duration, the use of this sampling rate for the rest of the ECG signal 300 would generate large amount of data. Therefore, controlling the sampling frequency of the ADC 210 (FIG. 2) and increasing this sampling rate according the behavior of the input signal 220 (FIG. 2) reduces the amount of data generated.

Figure 4:
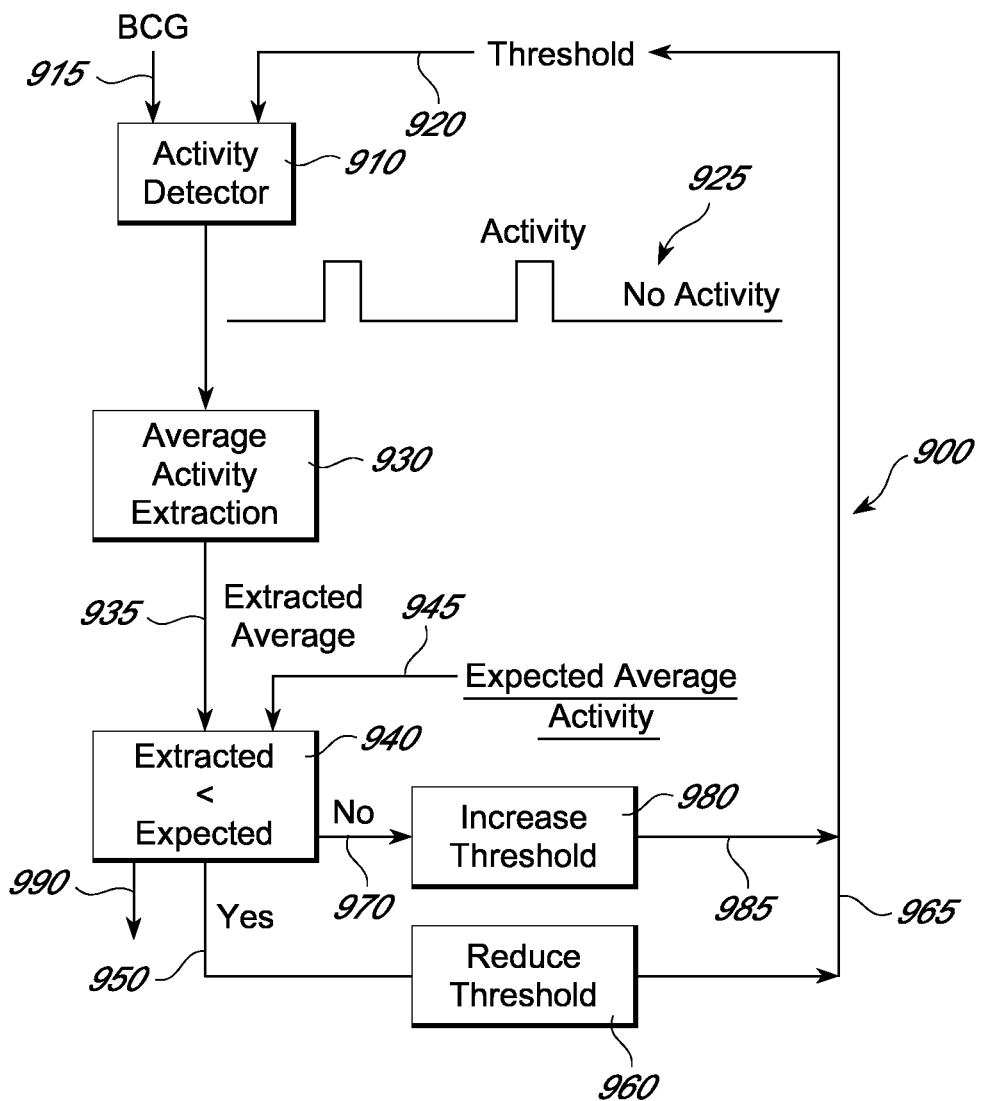
FIG. 4 illustrates a block diagram of the operation of an automatically variable threshold in accordance with one embodiment.

FIG. 4 illustrates a block diagram 900 of an automatically variable threshold system in one embodiment. The flow diagram 900 shows an activity detector 910 as described below with reference to for example FIG. 9. The activity detector 910 receives an analogue signal input 915 that corresponds to an ECG signal. It also receives a threshold input 920 that is determined as will be described below. The activity detector 910 determines activity of the analogue signal input 915 as shown by plot 925 and inputs the activity into an average activity extraction unit 930. The average activity extraction unit 930 determines the average of the activity 925 of the analogue signal 910 and provides an extracted average signal 935 to a comparator 940. A second input 945 to the comparator 940 corresponds to an expected average activity, the determination of which will be described below with reference to FIG. 5.

If the extracted average signal 925 is less than the expected average signal 945, an output signal 950 is generated that passes to a threshold reducing unit 960. Output signal 965 from the threshold reducing unit 960 then forms the threshold input signal 920 as shown.

If the extracted average signal 925 is greater than the expected average signal 945, an output signal 970 is generated that passes to a threshold increasing unit 980. Output signal 985 from the threshold increasing unit 980 then forms the threshold input signal 920 as shown. If the extracted average signal 925 is the same as the expected average signal 945, an output signal 990 is produced by the comparator 940. Output signal 990 is used to control sampling of the analogue ECG signal 915.

Figure 5:
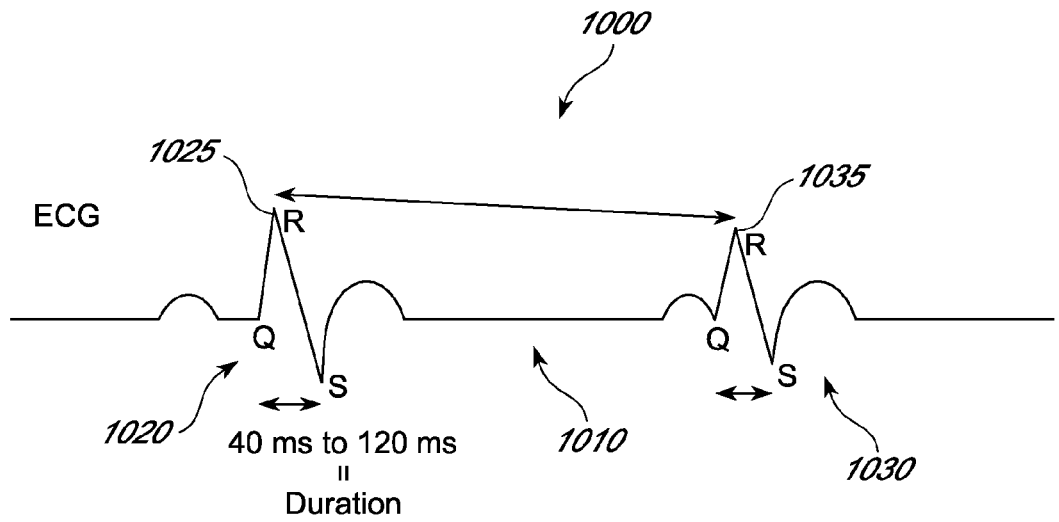
FIG. 5 illustrates the derivation of the expected average activity in the flow diagram of FIG. 9.

In FIG. 5, a diagram 1000 illustrating the derivation of the expected average signal 945 shown in FIG. 4 above. An ECG signal 1010 is shown that illustrates two QRS complex portions 1020 and 1030 respectively. The QRS complex is described above with reference to FIG. 3. The RR interval also corresponds to the duty cycle of QRS complex in the ECG signal. For a heart rate of 60 beats/min, the duty cycle is less than 12% and for a heart rate of 200 beats/min, the duty cycle is less than 40%.

The period between the R portions 1025 and 1035 of the two QRS complex portions 1020 and 1030 respectively is described as an 'RR interval' of the ECG signal 1010. The RR interval can be defined as the number of beats per minute (BPM) in the ECG signal 1010. From the RR interval, a value for the expected average can be determined from the maximum duration of a QRS complex portion and the RR interval:

Expected average activity=120 ms/RR interval or

Expected average activity=120 ms/(60/BPM)

The chosen value of 120 ms is the maximum duration of the QRS complex portion, but it will be appreciated that the minimum value of 40 ms or any value in between the minimum and the maximum can be chosen for the determination of the expected average activity.

Figure 6:
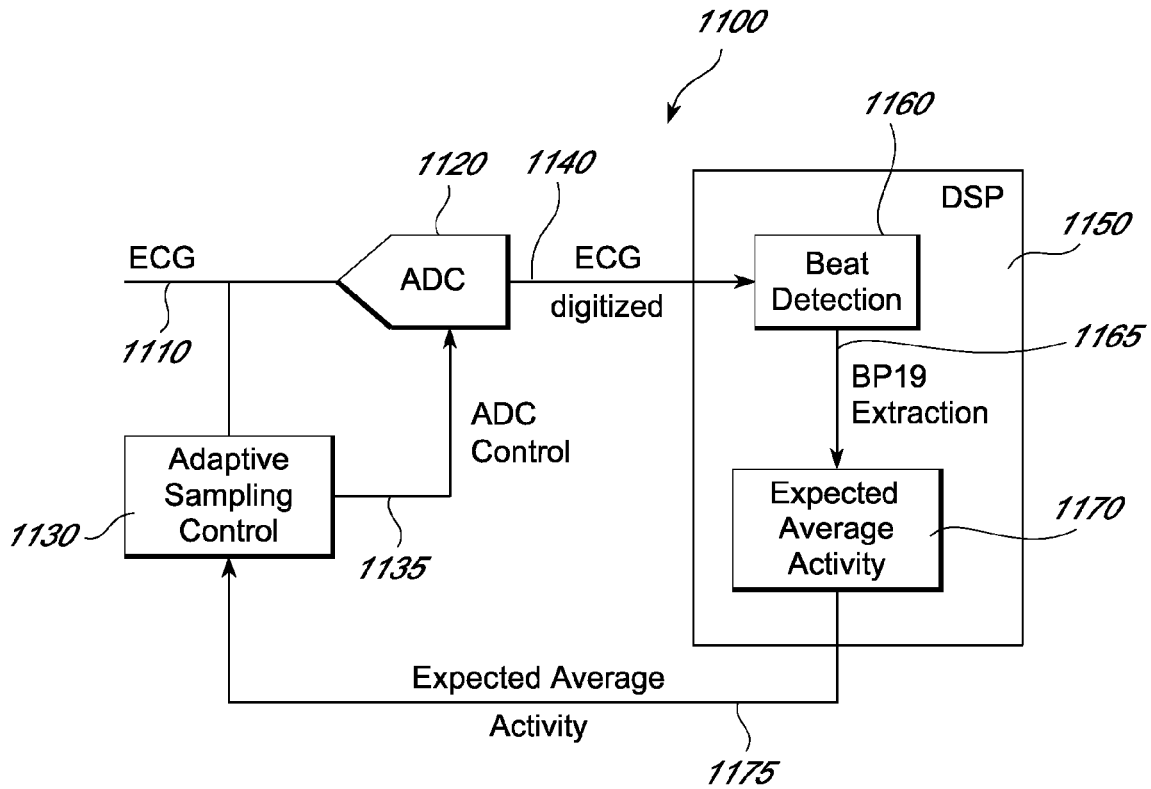
FIG. 6 illustrates a schematic block diagram of an implementation of an automatically variable threshold in accordance with one embodiment.

In FIG. 6, a block diagram 1100 of one implementation of the adaptive threshold in accordance with one embodiment is shown. An analogue ECG signal 1110 is shown that is input to an ADC 1120 and to an adaptive sampling control unit 1130. As discussed above, the ADC 1120 samples and digitizes the analogue ECG signal 1110 in accordance with a variable sampling rate that is derived using an adaptive threshold as described above with reference to FIG. 4.

Digitized output signal 1140 from the ADC 1120 is passed to a digital signal processor (DSP) 1150. The DSP 1150 includes a beat detection unit 1160 and an expected average activity unit 1170. The beat detection unit 1160 determines the beats per minute of the ECG signal and provides an output signal 1165 to the expected average activity unit 1170. The expected average activity unit 1170 uses the output signal 1165 to determine an expected average activity value 1175 that is fed to the adaptive sampling control unit 1130.

As described above with reference to FIG. 4, the adaptive sampling control unit 1130 uses the expected average activity value 1175 as input 945 for the comparator 940. Output control signal 1135 from the adaptive sampling control unit 1130 is used to control the sampling frequency of the ADC 1120 as shown in FIG. 6.

Figure 7:
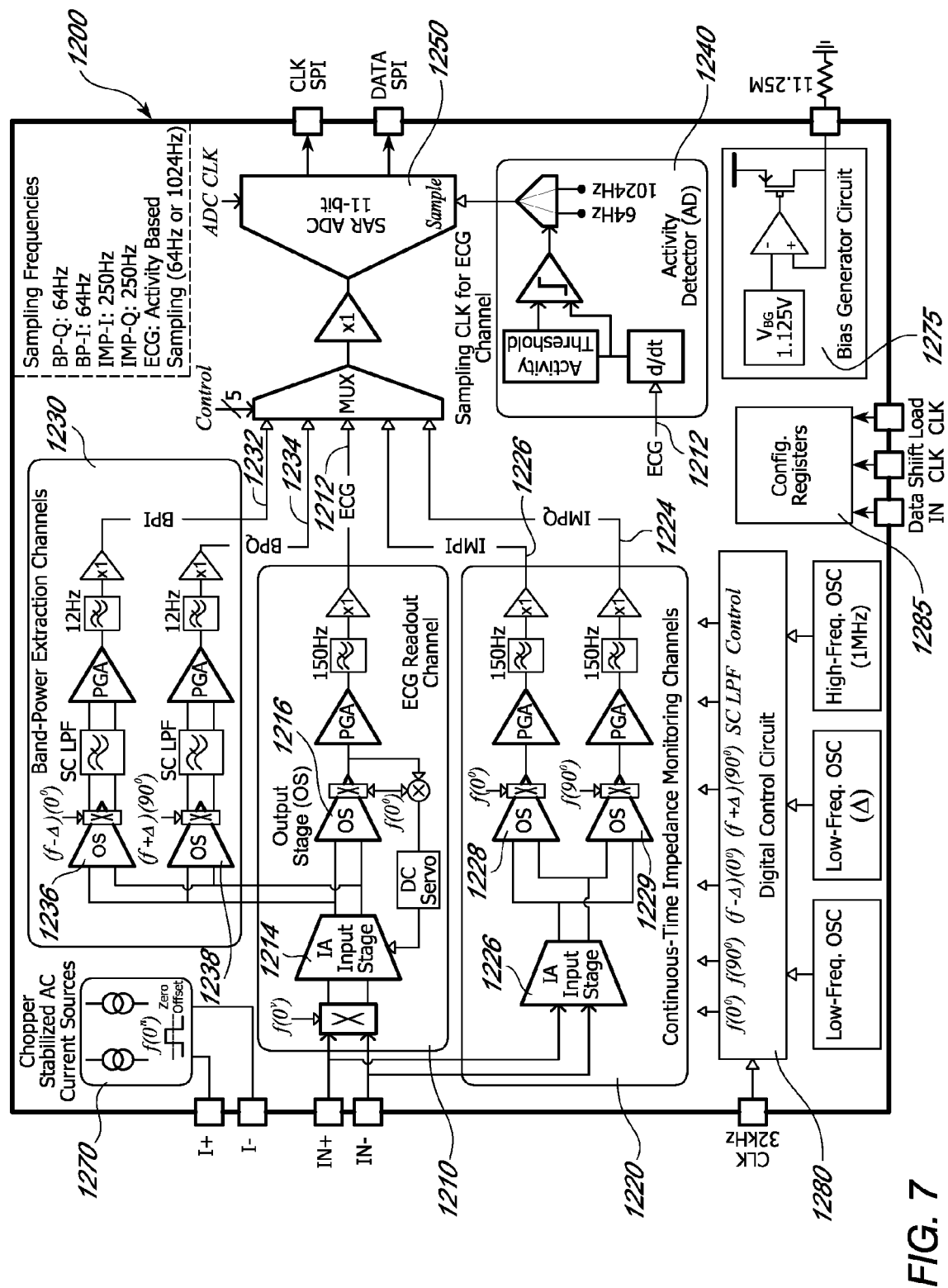
FIG. 7 illustrates a schematic diagram of an analogue signal processor (ASP) application-specific integrated circuit (ASIC) architecture in accordance with one embodiment.

Referring now to FIG. 7, an analogue signal processor (ASP) 1200 is shown. The ASP 1200 consists of an ECG readout channel 1210, a continuous-time impedance monitoring channel 1220, a band-power extraction channel 1230, an activity detector (AD) 1240, and an ADC 1250. The ECG readout channel 1210 provides an ECG output signal 1212. The continuous-time impedance monitoring channel 1220 provides two quadrature readout channels 1222, 1224 that are indicative of electrode-tissue impedance. The band-power extraction channel 1230 provides two quadrature readout channels 1232, 1234 for tracking power fluctuations in a specific frequency band. The AD 1240 receives the ECG output signal 1212 and senses its frequency content to adapt the sampling rate of ADC 1250.

The ASP 1200 comprises four major building blocks:
1. a low-noise and high common-mode rejection ratio (CMRR) readout channel for extracting ECG signals (ECG readout channel 1210);
2. two band-power extraction channels for extracting signal fluctuations in the specified frequency band (quadrature readout channels 1232, 1234 of band-power extraction channel 1230);
3. an impedance readout circuit for monitoring electrode-tissue contact impedance simultaneously with the biopotential signals (quadrature readout channels 1222, 1224 of continuous-time impedance monitoring channel 1220); and
4. an adaptive sampling ADC (AS-ADC) for reducing the equivalent data rate of the ECG readout channel 1210 (ADC 1250).

In addition, to these major building blocks, the ASP 1200 also includes two low-frequency oscillators at 8 kHz and a high-frequency oscillator at 1 MHz that form part of the digital control circuit 1280 as shown.

The operation of the ASP 1200 is as follows: the ECG readout channel 1210 extracts the biopotential signals, the output of which is sampled compressively by the AS-ADC 1250. This minimizes the equivalent output data rate of the ASP output which in turn reduces the power consumption of the DSP and the wireless data transmission as described above with reference to FIG. 1. Meanwhile, the band-power extraction channels 1230 implement a band-pass filter for extracting the signal fluctuations in the selected frequency band which enables the detection of ECG signal features with very low power consumption. Finally, a current stimulation block 1270 stimulates the electrode-tissue interface with an AC current. The resulting voltage is amplified by the impedance measurement channels to extract the imaginary and real components of the electrode-tissue contact impedance. This enables the system to continuously monitor the ECG signal integrity against lead connectivity and motion-induced signal artefacts.

The ECG readout channel 1210 uses a chopper stabilized instrumentation amplifier (IA) architecture 1214 for increasing the CMRR and reducing flicker noise as described in "Circuit Techniques for Reducing the Effects of Opamp Imperfections" by C C Enz and G C Temes, Proceedings of IEEE, vol. 84, no. 11, pages 1584 to 1614, November 1996.

It has been shown that tracking power fluctuations of EEG signals in a specific frequency band can be implemented in a power efficient manner ("A 5 μW/Channel Spectral Analysis IC for Chronic Bidirectional Brain-Machine Interfaces" by A-T Avestruz, W Santa, D Carlson, R Jensen, S Stanslaski, A Helfenstine and T Denison, IEEE J. of Solid-State Circuits, vol. 43, no. 12, pages 3006 to 3024, December 2008, which is incorporated herein by reference). The band-power extraction channel 1230 includes quadrature readout channels similar to that described in that article with an adjustable demodulation frequency, f+Δ, to shift the frequency of interest into the bandwidth of switched-capacitor (SC) low-pass filters (LPF) as shown.

However, the key difference is the use of a single IA input stage 1214 in the ECG readout channel 1210 from which the quadrature paths in the band-power extraction channel 1230 are derived. This presents an important advantage over that described in the article above in terms of the efficient use of power as a separate IA is not required for each signal path. The input stage of the presented IA consumes 1.2 μA from 2V, while achieving 86 nV/√Hz input referred noise density, whereas each output stage (OS) consumes 400 nA with negligible noise contribution. This translates into a noise-efficiency-factor (NEF) of 4.7 as described in "A Low-Power Low-Noise CMOS Amplifier for Neural Recording Applications" by R R Harrison and C Charles, IEEE J. of Solid State Circuits, vol. 38, no. 6, pages 958 to 965, June 2003, which is incorporated herein by reference. However, the effective NEF is much lower, since functionality can be increased without the requirement of an additional IA input stage.

Returning now to FIG. 7, the ASP 1200 also includes a multiplexer (MUX) 1260 through which the ECG output signal 1212, the two quadrature readout channels 1222, 1224 from the continuous-time impedance monitoring channel 1220 and the two quadrature readout channels 1232, 1234 from the band-power extraction channel 1230 are fed. The ASP 1200 also includes chopper stabilized AC current sources 1270, a bias generator circuit 1275, a digital control circuit 1280 and configuration registers 1285.

The chopper stabilized AC current sources 1270 provides stabilized current supply to the ASP 1200 where it is needed. The digital control circuit 1280 provides the frequency controls for the ECG readout channel 1210, the continuous-time impedance monitoring channel 1220, and the band-power extraction channel 1230 as shown.

The ASP 1200 comprises two input stages (IS), namely, IS 1214 in ECG readout channel 1210 and IS 1226 in continuous-time impedance monitoring channel 1220, that are connected to five output stages (OS), namely, OS 1216 in ECG readout channel 1210, OS 1236, 1238 in band-power extraction channel 1230, and OS 1228, 1229 in continuous-time impedance monitoring channel 1220. As shown, IS 1214 is connected to OS 1216, 1236 and 1238. This way of using a single IS with multiple OS for implementing signal paths utilizing the same signal source but implementing different functionalities is enabled by using a current-balancing transconductance stage, similar to that described in "A 200 μW Eight-Channel EEG Acquisition ASIC for Ambulatory EEG Systems" by RF Yazicioglu, P Merken, B Puers and C Van Hoof, IEE J. of Solid-State Circuits, vol. 43, no. 12, pages 3025 to 3038, December 2008, which is incorporated herein by reference. The replicas of OS can be connected to OUTP (positive output) and OUTN (negative output) in parallel, for instance, with different demodulation clock frequencies. Since the demodulators are present at low-impedance nodes of the OS, the different clocking schemes of the OS have minimal effect on one another.

Input and output stages described above may be implemented using an instrumentation amplifier as described in EP-A-2086111.

Figure 8:
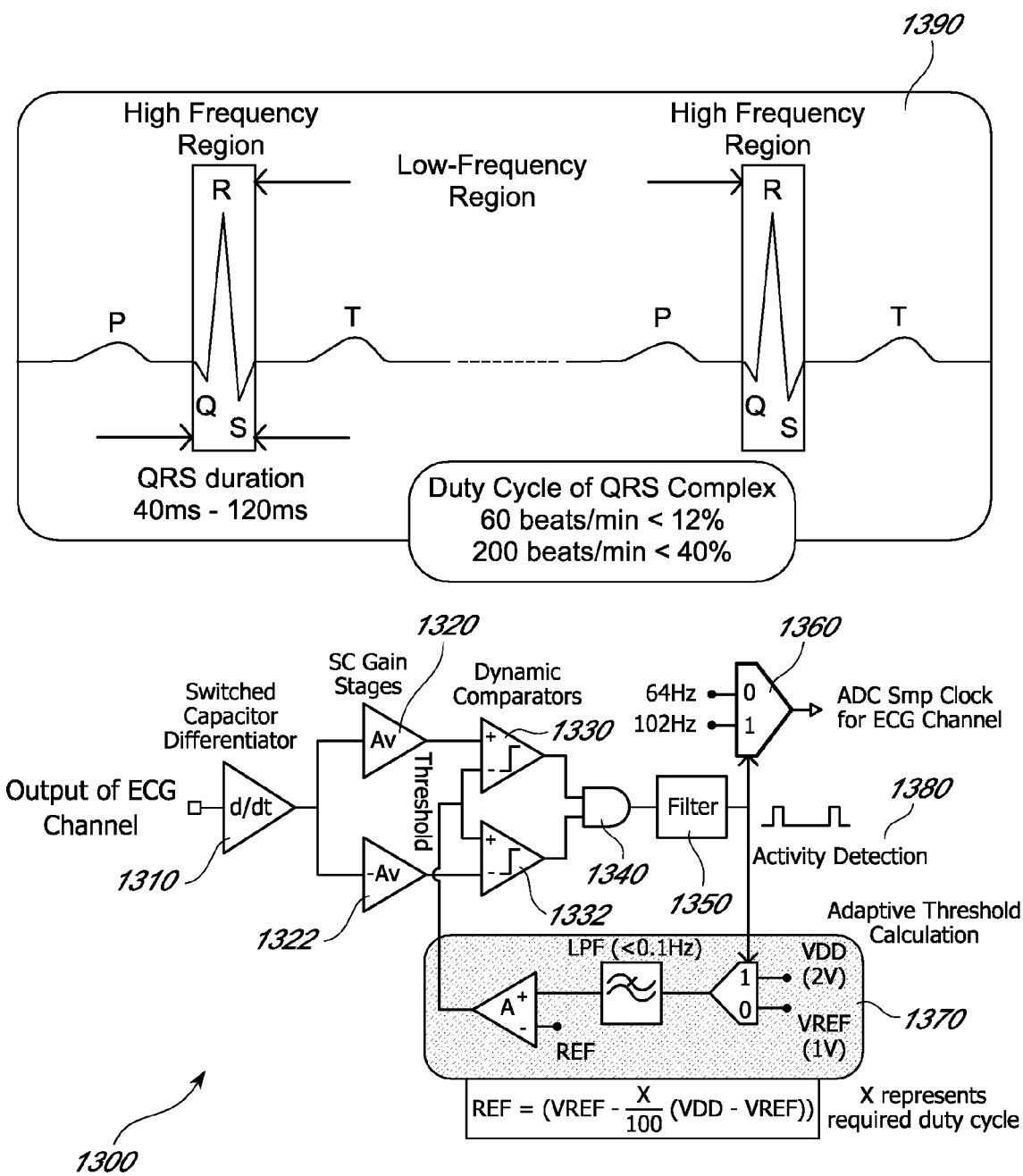
FIG. 8 illustrates a schematic diagram of an implementation of an activity detection circuit together with an ECG signal waveform.

FIG. 8 shows the architecture of an activity detector (AD) circuit 1300 for adaptively sampling the ECG signal and reducing the equivalent data rate. The AD circuit 1300 is more detailed than the AD 1040 shown in FIG. 5.

The AD circuit 1300 comprises a switched capacitor (SC) differentiator 1310 that receives at its input the output 1012 from the ECG channel 1010 shown in FIG. 5. The differentiator 1310 is connected to two SC gain stages 1320, 1322 and to two dynamic comparators 1330, 1332 as shown. The outputs from the dynamic comparators 1330, 1332 are passed to an AND gate 1340 before being filtered in filter 1350 to provide an input to a sample clock selector 1360. The sample clock selector 1360 controls the sampling of the ECG signal 1012 from the ECG channel 1010 as discussed above by switching between a standard, low clock frequency of 64 Hz and a high clock frequency of 1024 Hz when the QRS complex is detected. An adaptive threshold calculator 1370 is connected to apply a threshold to the dynamic comparators 1330, 1332 that is derived from the signal supplied to the sample clock selector 1360.

The SC differentiator 1310 scales the input ECG signal according to its frequency content. The output is amplified (SC gain stages 1320, 1322) and compared (dynamic comparators 1330, 1332) against a threshold voltage to detect the presence of high-frequency activity during which the sampling rate of the ADC is increased from 64 Hz to 1024 Hz. This threshold voltage is derived from the threshold circuit (adaptive threshold calculator 1370) that forces the duty cycle of an AD output 1380 equal to a pre-set value of X. This value can be selected based on the heart rate and duration of a QRS complex bearing in mind that there is a possible presence of high frequency artefacts.

Inset 1390 in FIG. 8 shows the duty cycle of the QRS complex and the frequency of the clock signal applied to the ADC 1250 (FIG. 7).

Tables 1 and 2 below give summaries of measurements taken from the ASP 1200 (FIG. 7). Table 1 gives the power breakdown of the building blocks of the ASP 1200, and Table 2 gives the ASIC values as well as a summary of the ASIC measurements. As shown, the ASP 1200 consumes less than 13.5 μA from a 2V supply with AD block turned on.

TABLE 1

Power Breakdown of the Building Blocks

| | |
|---|---|
| Analog Readout Front-End | 5.3 μA |
| IA Input Stage | 1.2 μA |
| IA Output Stage - Single Ended | 400 nA |
| IA Output Stage - Differential | 350 nA |
| Bias Circuit | 2 μA |
| Low Frequency Oscillators | 0.65 μA |
| ADC Buffer | 0.45 μA |
| Activity Based Sampling | 0.4 μA |
| Chopper Stab. AC Current Generation | 0.45 μA |
| ADC + SPI | 1.1 μA/kHz |
| HF | 0.7 μA |
| Total Current (Activity Based Sampling OFF) | 15.25 μA |
| Total Current (Activity Based Sampling ON) | 13.25 μA |

TABLE 2

Summary of the ASIC Measurement Results

| | |
|---|---|
| Supply Voltage | 2 V |
| Current Consumption (Activity based sampling ON) | 13.25 μA |
| Current Consumption (Activity based sampling OFF) | 15.25 μA |
| Common-Mode Rejection Ratio (with floating HPF) | >105 dB |
| Input Referred Noise (ECG Channel) | 85 nV/$\sqrt{Hz}$ |
| Input Referred Noise (Imp. Measurement) | 1.7 Ω/$\sqrt{Hz}$-9 Ω/$\sqrt{Hz}$ |
| Gain (ECG Channel) | 300, 500, 900, 1300 |
| Bandwidth (ECG Channel) | 170 Hz, 140 Hz |
| Gain (Impedance Channels) | 300, 500, 900, 1300 |
| Bandwidth (Impedance Channels) | 50 Hz |
| Gain (Band-Power Extraction Channels) | 810, 1620, 3240 |
| Bandwidth (Band-Power Extraction Channels) | 4.6 Hz-6.8 Hz with adjustable center frequency (set to 16 Hz during measurements) |

Figure 9:
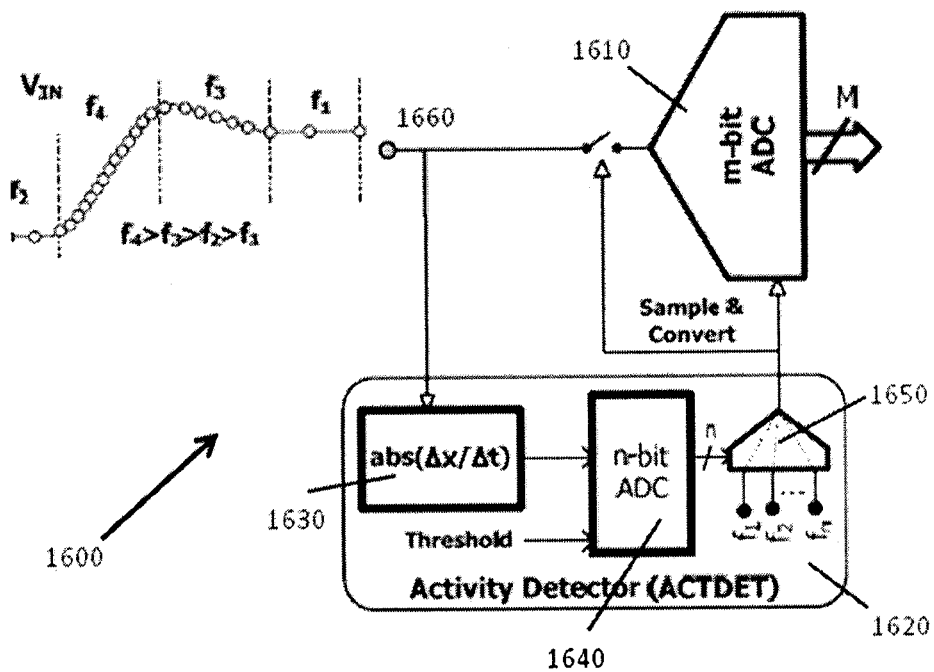
FIG. 9 illustrates an architecture for adaptive sampling ADC (AS-ADC) according to one embodiment.

FIG. 9 shows an architecture 1600 of the adaptive sampling ADC (AS-ADC) according to one embodiment. The architecture 1600 comprises two major blocks, namely, an m-bit ADC 1610 and an activity detector (ACTDET) 1620. As described above, the ACTDET 1620 senses the activity of the input signal and adapts the sampling rate of the ADC 1610 accordingly. The ACTDET 1620 consists of a differentiator 1630, an n-bit ADC 1640 (or any means arranged for quantizing the rate of change information from an analogue input signal known by the person skilled in the art), and a sampling clock frequency selector 1650. The differentiator 1630 extracts the rate of change information from an input signal 1660, which is quantized by the n-bit ADC 1640 within the ACTDET 1620. The sampling rate, which is assigned to each quantization level, is selected based on the output of the n-bit ADC 1640. Thus, the input signal 1660 can be sampled with an adaptive sampling rate depending on the rate of change of the input signal.

This implementation can be seen as an intermediate approach between a conventional ADC, where the sampling time is exact but the voltage levels are quantized, and asynchronous level-crossing ADCs as discussed in "A 0.8V Asynchronous ADC for Energy Constrained Sensing Application" by M Trakimas and S Sonkusale, IEEE CICC, pages 173 to 176, September 2008, which is incorporated herein by reference, where the voltage levels are exact but the time samples are continuous. The former suffers from the large number of samples due to the selection of the sampling rate according to the highest frequency signal which is not necessarily always present, while the latter has the difficulty to be used with a standard DSP platform due to the continuous nature of the sampling rate so a dedicated DSP platform is required. This architecture implements data reduction with the possibility to process this data directly in a standard DSP platform.

The adaptive sampling ADC can use a standard successive approximation (SAR) ADC as the core. The ADC uses the split-DAC architecture to implement an 11-bit DAC with small silicon area. Additionally, the self-timed bit cycling approach has been employed in order to relax the settling time of the comparator. In order to enable rail-to-rail input range, a level shifter sampling approach can be used. The reference voltage for the ADC is generated by using a switched capacitor divider that generates $V_{DD}/2$ as the reference voltage from the supply voltage using a replica of the SAR DAC. The unit capacitance of the DAC is 400 fF, which sets the total input capacitance of the ADC to 25.6 pF. The choice of a relatively large unit capacitance is driven by the matching characteristics of the poly-poly capacitors, enabling 11-bit resolution in DAC voltage steps across ±3σ mismatches.

Figure 10:
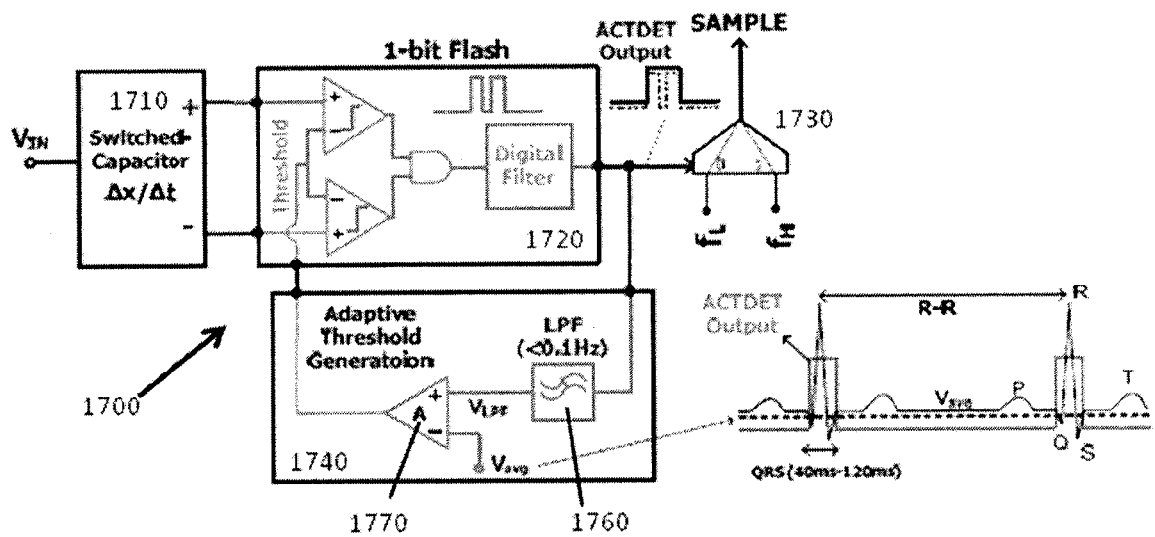
FIG. 10 illustrates a block diagram of a possible architecture for the activity detection block.

Referring now to FIG. 10, a more detailed view of the ACTDET 1620 of FIG. 9 is shown. ACTDET 1700 comprises a switched capacitor (SC) differentiator 1710 connected to a 1-bit flash ADC 1720 which provides an output that is used to select the sampling frequency in a sampling clock frequency selector 1730. The output is also used for an adaptive threshold generator 1740 as shown.

An input signal $V_{IN}$ is first differentiated by using the SC differentiator 1710 and the output digitized by the single-bit flash ADC 1720, passed through a digital filter and the output is used to select the sampling rate of the SAR ADC (not shown in FIG. 10). For simplicity of implementation only two frequency levels, "$f_L$" and "$f_H$", which represents the low and high frequency sampling rates of the ADC are shown. For example, the selection of 1024 Hz sampling rate for $F_H$ increases the time resolution of the R peak, whereas 64 Hz is sufficiently large with respect to the frequency content of P and T waves.

The ACTDET uses a differentiator at the front-end to extract the input signals rate of change. This choice of detecting the frequency using a differentiator stems from the fact that the use of filters to sense the activity of the input signal leads to significant group delay at the output of the filter according to:

$$\tau = \frac{\omega_0}{\omega_0^2 + \omega^2}$$

where $\omega_0$ is the −3 dB angular frequency of a filter and $\omega$ is the angular frequency of the input signal. This, in turn, leads to a delay in the selection of the sampling frequency. On the other hand, the group delay of an ideal differentiator is zero. Hence, the implemented ACTDET block uses a SC differentiator architecture (FIG. 10). The clock frequency of the SC differentiator is 250 Hz. In order to increase the update rate of the output, the actual implementation uses two differentiators operating at complementary clock phase. Such an implementation gives a maximum group delay of around 2.5 ms, which can be sufficient considering that high frequency sampling of ECG signals can be 256 Hz.

Another important issue is the selection of the threshold voltage. The amplitude and morphology of ECG signals vary significantly, leading to variations in the rate of change information, and requiring the use of an adaptive threshold. The threshold voltage of the 1-bit flash needs to be adapted in order to detect the high and low activity regions under changing input voltage amplitudes. For ECG applications, the high frequency regions can be considered as the QRS complex of the ECG signal as described with reference to FIG. 3 above. Therefore, in an ideal operation, it is required that the ACTDET output selects the high sampling rate $f_H$ during the presence of the QRS complex. The comparator output pulse should have the same duration and period as the QRS complex of the ECG signals. The average of the ideal ACTDET output pulse (or the duty cycle of the comparator output pulse) can be represented by $V_{AVG}$ and this average can be calculated since the width of the QRS complex is known. It should be noted that $V_{AVG}$ actually corresponds to the duty cycle of the QRS complex in the complete ECG signal. This can be calculated from the heart rate information extracted through, for example, a beat detection algorithm and/or the morphological definition of the QRS width, which is between 40 ms and 120 ms.

Therefore, the threshold voltage of the ACTDET can be calculated forcing the duty cycle of the actual ACTDET output to match with the calculated $V_{AVG}$. The negative feedback loop from the output of the ACTDET to the input of the 1-bit flash 1720, first computes the average of the ACTDET output block using a low-pass filter (LPF) 1760 and then compares this average, $V_{LPF}$, to $V_{AVG}$, in a comparator 1770 so that the threshold voltage can be regulated to match $V_{LPF}$ to $V_{AVG}$. After settling $V_{LPF}=V_{AVG}$, the threshold of the comparator stage 1770 can be set to increase the ADC sampling frequency only during the QRS complex. The transfer function from the input of the SC differentiator to the output of the low-pass filter can be written as:

$$V_{LPF}(s) = \frac{s_p}{s + (1+A)s_p}[V_{IN}(s)H(s) + AV_{AVG}]$$

where H(s) is the transfer function of the SC differentiator 1710, $s_p$ the cut-off frequency of the LPF 1760 and A is the gain of the feedback amplifier. The LPF 1760 can be implemented by an RC filter, where the resistor element, R, is implemented using a pseudo resistor. This enables the implementation of a low-pass filter with very low cut-off frequency, or in other words, it enables the average of the ACTDET output to be taken over a long period. On the other hand, the use of a large loop gain (for example A=10) sets $V_{LPF}$ to $V_{AVG}$ and reduces the effect of the SC differentiator output on the threshold voltage.

Figure 11:
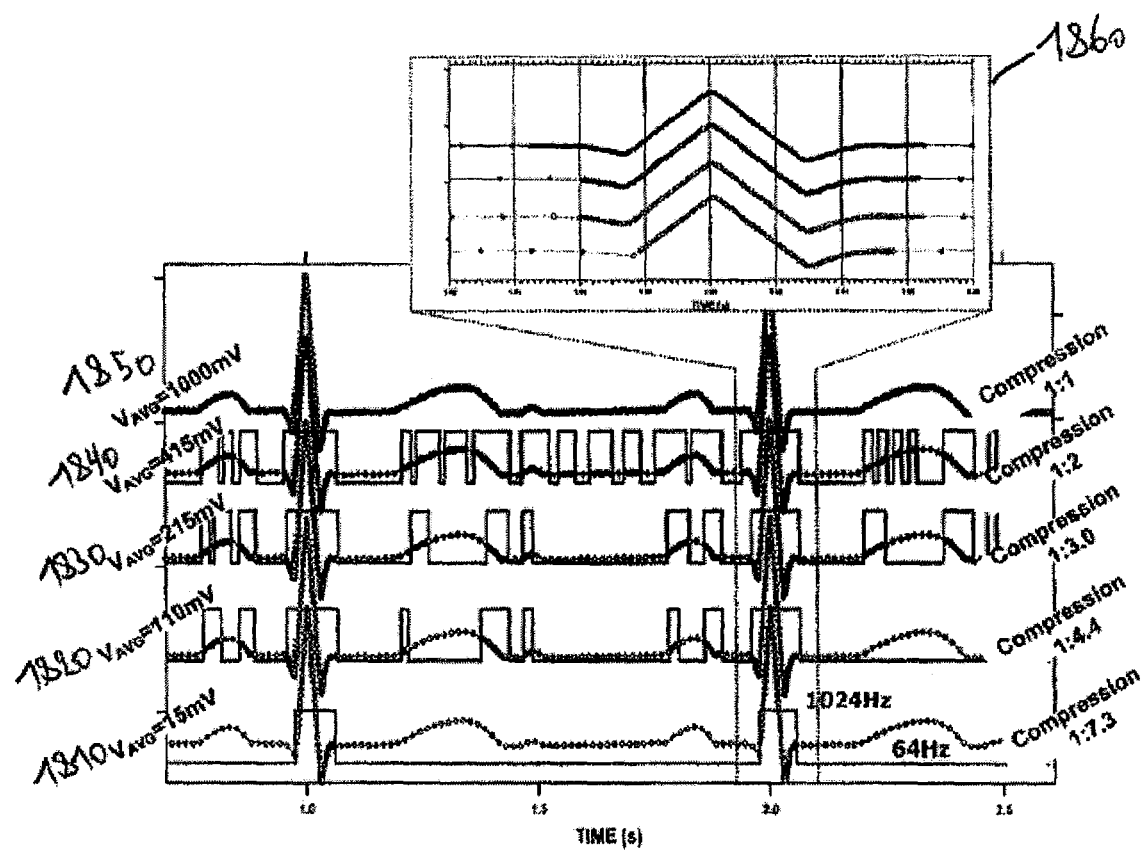
FIG. 11 illustrates the variation in ECG signals at different compression ratios.
Figure 13:
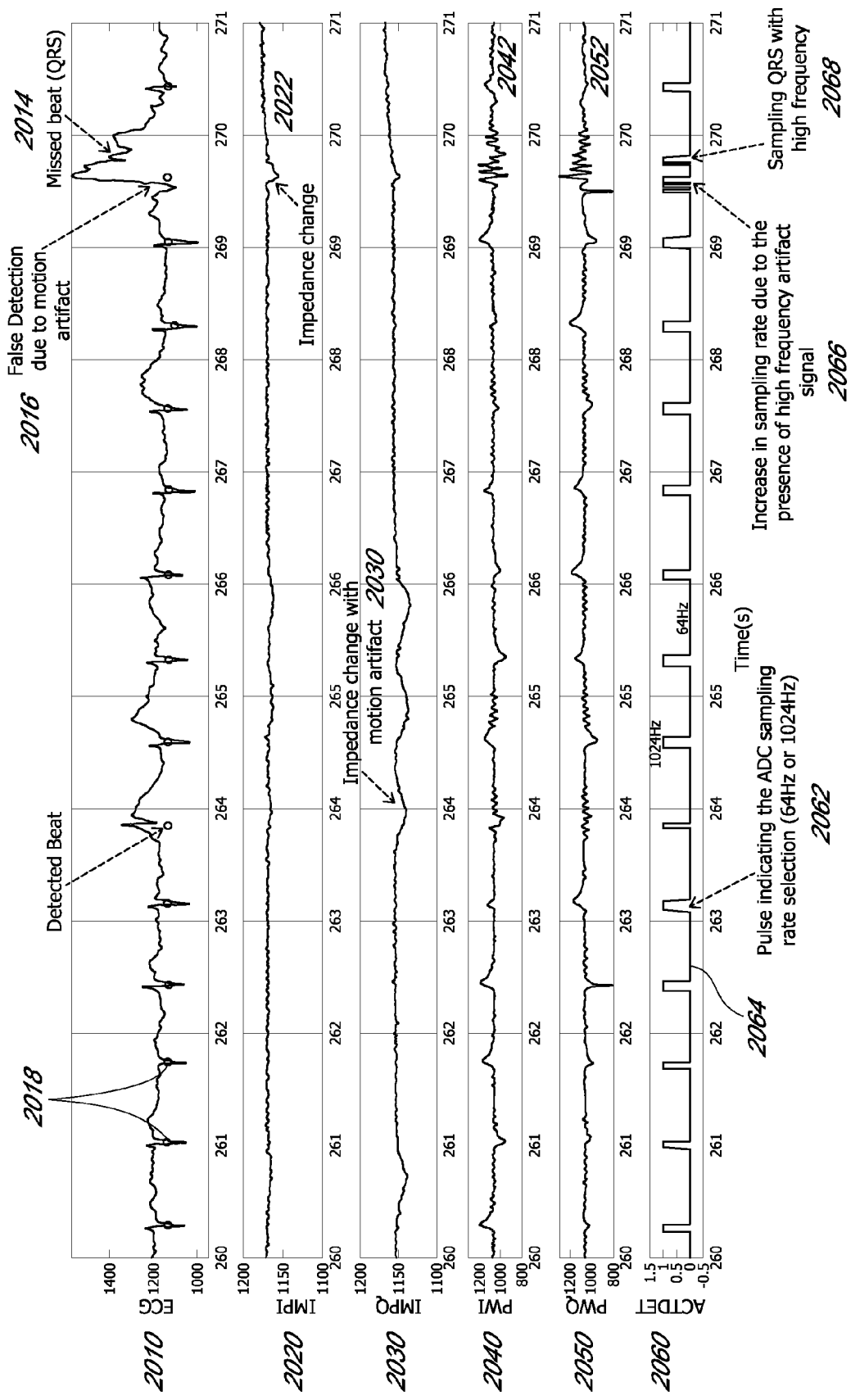
FIG. 13 illustrates measured results of a wireless ECG monitoring system in accordance with one embodiment.

FIG. 11 shows the effect of changing the $V_{AVG}$ while sampling a synthetic ECG signal at 60 beats-per-minute. The real life operation is shown in FIG. 13 and discussed below. The ideal value of the comparator output duty cycle is calculated to be between 4% and 12% as the QRS complex width is between 40 ms and 120 ms, and the average beat-to-beat duration is 1 s.

For the first measurement, trace 1810, $V_{AVG}$ is selected as 15 mV causing the ADC to increase the sampling rate from 64 Hz to 1024 Hz only during the presence of the QRS complex. As $V_{AVG}$ is increased to 110 mV, 215 mV and 415 mV, the duty cycle of the high frequency sampling rate is also increased as shown by respective traces 1820, 1830, 1840 and 1850. The compression obtained for each value of $V_{AVG}$ is 1:7.3, 1:4.4, 1:3.0, 1:2 and 1:1 respectively. Inset 1860 in FIG. 11 illustrates the delay between the start of the QRS complex and switching to high frequency sampling rate at each of the values for $V_{AVG}$.

In order to characterize the operation of the AS-ADC, a sinusoidal signal (or any periodical signal known in the art) is fed to the input of the ADC and the duty cycle of the comparator output pulse is monitored, while changing the $V_{AVG}$ input of the ACTDET block. The effect of this is shown in FIG. 12.

Figure 12:
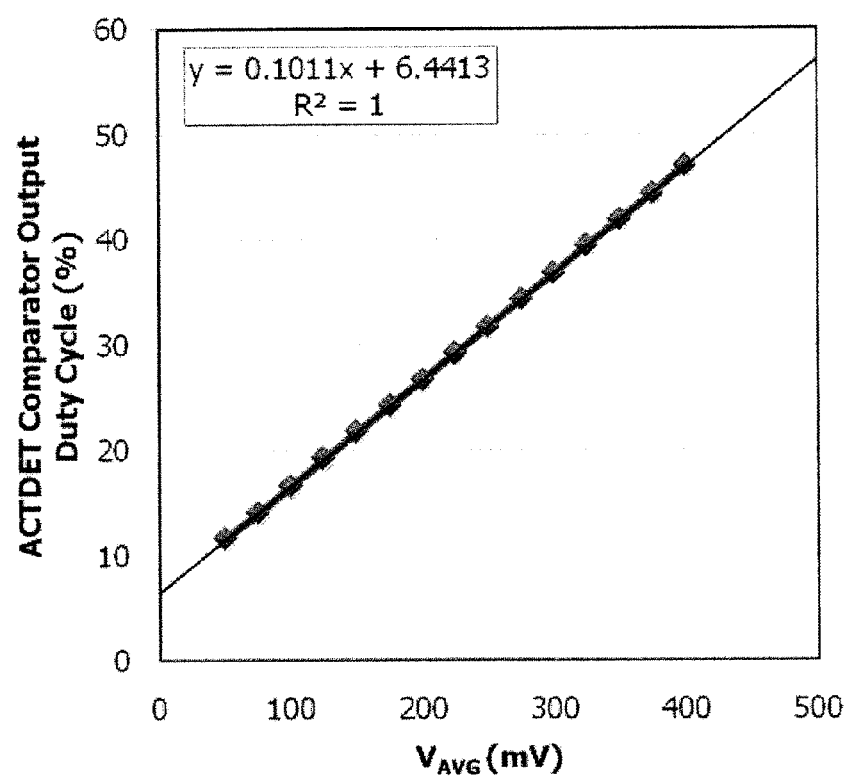
FIG. 12 illustrates a graph showing the linear relationship between the duty cycle of a comparator output pulse and an input $V_{AVG}$.

FIG. 12 shows the linear relation between the duty cycle of the comparator output pulse and the input $V_{AVG}$. This enables the user to set the width of the comparator output pulse to the ideal width of the QRS complex once the average beat-to-beat interval is known.

This activity based sampling ADC architecture has been implemented in a 0.5 μm CMOS process as a part of an analogue signal processor ASIC dedicated to ECG signal extraction and processing applications and operates from a 2V supply. The ADC consumes 2.2 μA average current at a conversion speed of 2 kS/s and the power dissipation decreases linearly as the sampling frequency decreases. The implemented ACTDET block dissipates 400 nA of additional current. The DC characterization of the ADC shows that the DNL (difference between a step and an ideal value) is less than 0.3 LSB and the INL (deviation of the transfer function from a straight line) is less than 0.5 LSB. The signal-to-noise and distortion ratio (SINAD) of the ADC is measured as 65.4 dB.

The adaptive sampling ADC has been tested first with synthetic signals and then with the real ECG signals. The traces 1810, 1820, 1830, 1840 and 1850 shown in FIG. 11 relate to synthetic signals, in particular, the output of the implemented ADC with a 60 bpm synthetic ECG signal. The traces shown each indicates the sampling of the ECG with a constant sampling rate tailored according to the frequency of the QRS complex. To set the adaptive sampling operation, the duty cycle of the QRS complex is calculated from the maximum width of the QRS complex (120 ms) and the period of the ECG beat (1 second) as 12%. This corresponds to a $V_{AVG}$ of 240 mV considering that the output of the ACTDET is a pulse between 0 and 2V. The $V_{AVG}$ is changed from 2V down to 240 mV showing the operation of the adaptive sampling of the ECG signals. It should be noted that the exact value of $V_{AVG}$ is not important and higher than ideal $V_{AVG}$ (240 mV) only makes the ADC sample slower regions with high sampling rate.

For the operation of the ADC in a real monitoring application, $V_{AVG}$ is set to 20% duty cycle for the ACTDET output pulse. The ADC increases its sampling rate during the QRS complex and the high activity regions (motion artefact signals). Due to the averaging over a long period, the presence of motion artefacts does not affect the sampling of the QRS complex with high sampling rate. This sampling scheme leads to a five times improvement on the average data rate, which can significantly reduce both the processing and the wireless transmission power dissipation. It should also be noted that as the equivalent conversion rate of the ADC is reduced through activity based sampling, the power dissipation of the ADC linearly scales from 2.2 µA as the overall data rate is reduced.

FIG. 13 shows the signals at different points within the ASP 1000 in accordance with one embodiment for a real life situation. Trace 2010 relates to the actual ECG signal that is received. Traces 2020 and 2030 relate respectively to the I and Q components provided by the continuous-time impedance monitoring channel 1020 in FIG. 5. Traces 2040 and 2050 relate respectively to the I and Q components provided by the band-power extraction channel 1030 in FIG. 5. Trace 2060 relates to the operation of the activity detector 1040 in FIG. 5.

In trace 2010, detected beats 2012 are shown together with a missed beat 2014 and a false detection 2016 due to the presence of a motion artefact. In trace 2020, an impedance change 2022 is shown and in trace 2030, an impedance change 2032 with motion artefact is shown. Changes 2042 and 2052 are shown in respective traces 2040 and 2050 that correspond to the missed beat 2014 and/or the false detection 2016.

In trace 2060, a pulse 2062 indicates the ADC sampling rate selection of the higher rate of 1024 Hz when a beat 2012 is detected. Lines 2064 between the pulses 2062 correspond to the lower rate of 64 Hz. Also shown are pulses 2066 and 2068 that correspond to an increase in sampling rate due to the presence of a high frequency artefact signal and a sampling QRS with high frequency respectively.

The key benefit of such an adaptive sampling scheme is its effect on the average data rate that the system needs to process and/or transmit over the radio or wireless link. In general, wireless sensor nodes follow two approaches for the continuous monitoring of biopotential signals:—
1. signals are processed in the system and result is transmitted; and
2. signals are continuously streamed and the processing takes place at the receiver side.

The former suffers from the large power dissipation in the DSP, where as the latter leads to significant power dissipation in the radio or wireless link.

The use of continuous wavelet transform (CWT) has been demonstrated to be very reliable for the processing of ECG signals in "Low-Power Robust Beat Detection in Ambulatory Cardiac Monitoring" by I Romero et al, IEEE BioCAS, pages 249 to 252, November 2009, which is incorporated herein by reference. However, such use leads to large power dissipation in the DSP due to the complexity of the algorithm and the high data rate. In order to quantify the benefits of certain embodiments, the algorithm described in the above mentioned article was integrated into a commercial low-power microcontroller (µC) (MSP430). The ECG signal, adaptively sampled by an ADC in accordance with one embodiment, was fed to an algorithm tailored to process adaptively sampled ECG signals ($f_L$=64 Hz and $f_H$=256 Hz). The only modification that was done was to the front-end of the algorithm, that is, the convolution of the ECG signal with a mother wavelet.

Figure 14:
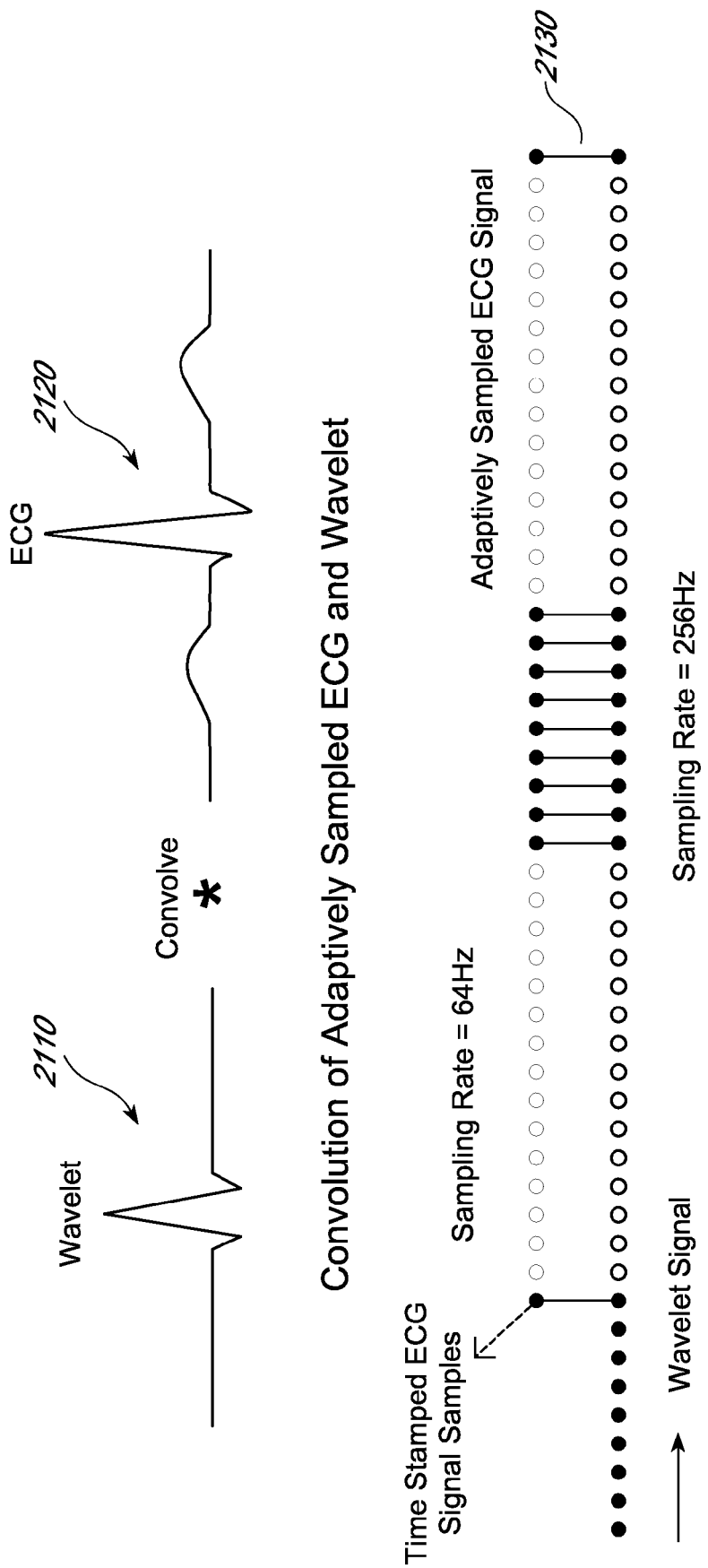
FIG. 14 illustrates the application of a continuous wavelet transform to an adaptively sampled ECG signal.

As shown in FIG. 14, adaptive sampling significantly reduces the number of multiplications and the memory access during the convolution. Here, a wavelet 2110 was convolved with an adaptively sampled ECG signal 2120 only in the region of the QRS complex was convolved to provide an output as shown at 2130. Output 2130 shows the lower sampling rate of 64 Hz where there was no QRS complex and the higher sampling rate of 256 Hz where there was a QRS complex.

Figure 15:
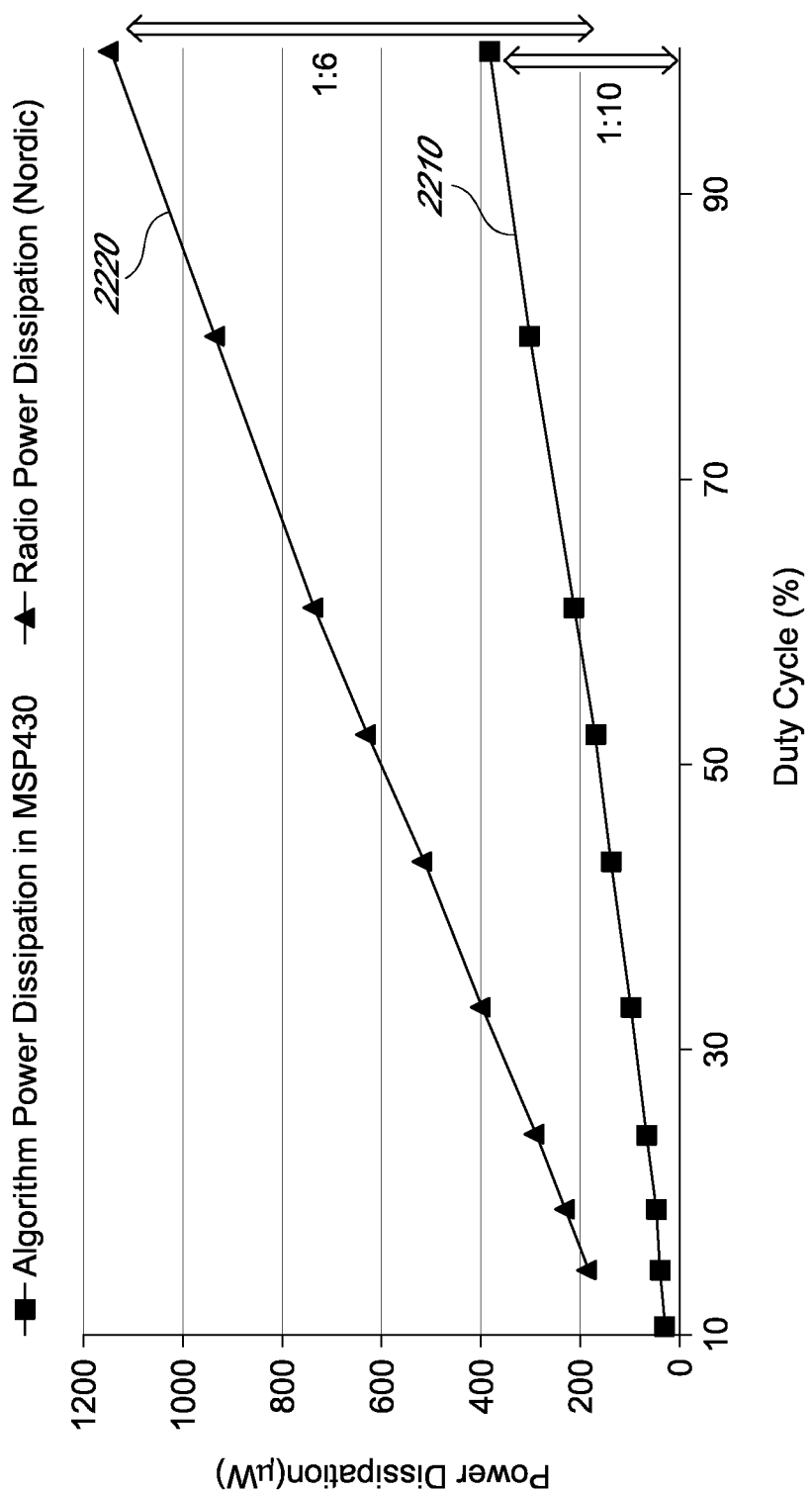
FIG. 15 illustrates power dissipation of the processor and the wireless link as a function of the duty cycle.

FIG. 15 shows the measurement of the power dissipation in the processor as the data rate of the ECG signal is reduced using adaptive sampling. The power dissipation of the processor, indicated by line 2210, using adaptive sampling equivalent to 15% data rate of the full 100% sampling rate corresponds to ten times reduction in the power dissipation for processing the ECG signal with 70 bpm.

A similar test platform has been implemented for the continuous streaming of the ECG data through a commercial low-power radio (Nordic). The adaptively sampled ECG signal ($f_L$=64 Hz and $f_H$=1024 Hz) is time-stamped and streamed over the radio or wireless link. FIG. 15 also shows that the power dissipation, indicated by line 2220, of the radio or wireless link is reduced by a factor more than six as the equivalent data rate of the ECG signal is reduced by adaptive sampling ADC.

Figure 16:
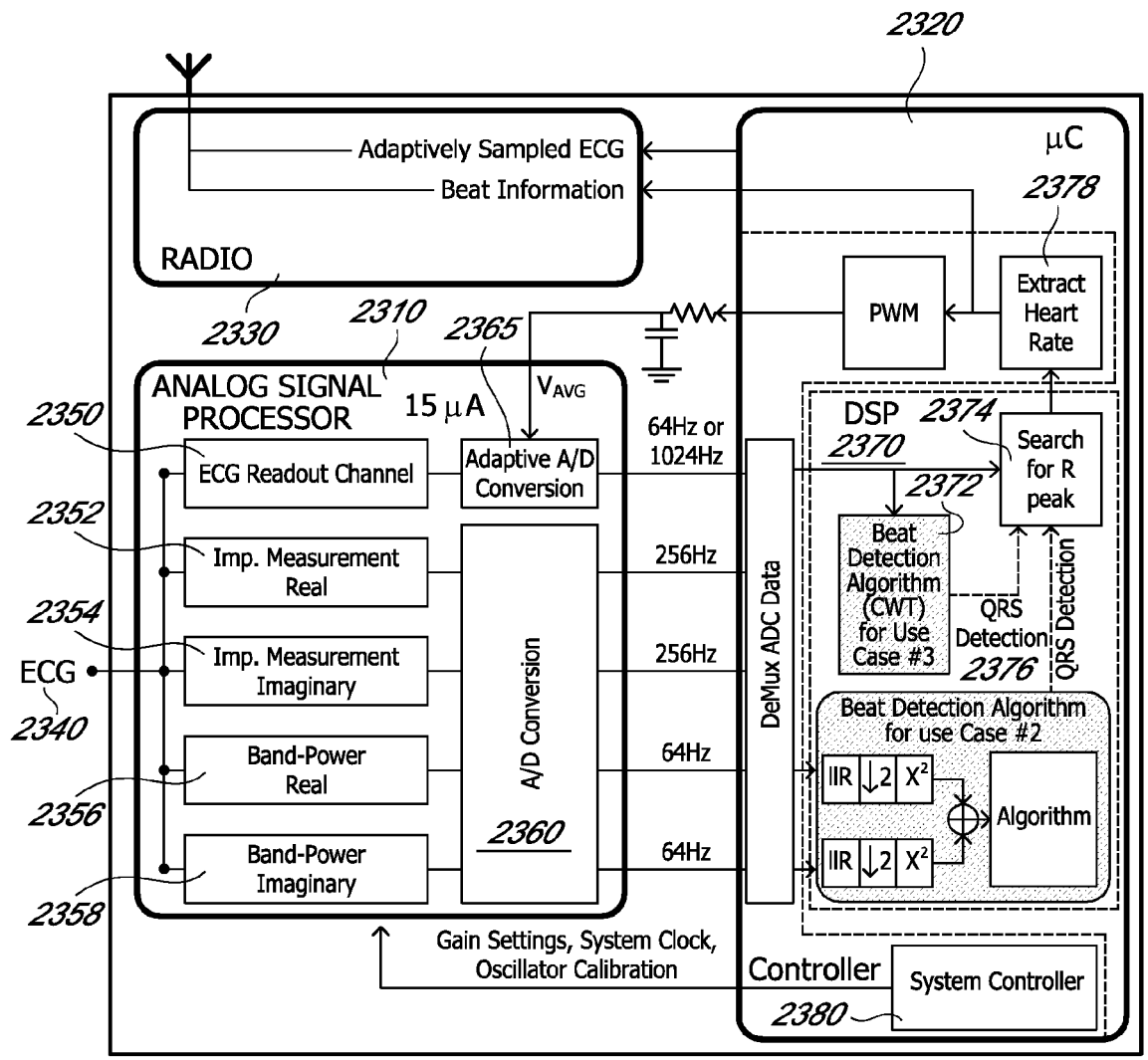
FIG. 16 illustrates an architecture of wireless ECG monitoring using an ASP in accordance with one embodiment.

As shown in FIG. 16, the ASP 2310 receives an input ECG signal 2340 that is processed by an ECG readout channel 2350, impedance measurement channels (real and imaginary) 2352, 2354, and band-power measurement channels (real and imaginary) 2356, 2358. Outputs from the impedance measurement channels 2352, 2354, and band-power measurement channels 2356, 2358 are passed to an ADC 2360 which samples the impedance measurement channels at 256 Hz and the band-power channels at 64 Hz. An adaptive sampling ADC 2365 is used for the ECG readout channel 2350 under the control of a $V_{AVG}$ signal from the µAC 2320 at either 64 Hz or 1024 Hz as described above. The digitized signals are passed to a DSP 2370 where they are processed to provide beat detection 2372 and R peak location 2374. QRS detection 2376 is also carried out to provide an input for the R peak location 2374. The output from the R peak location 2374 is used to extract the heart rate 2378 for controlling the adaptive ADC 2365 and for transmission to a receiver (not shown) by means of the radio 2330. The µU 2320 also includes a system controller 2380 that provides control settings, for example, gain settings, system clock and oscillator calibration, for the ASP 2310.

Not only do certain embodiments provide a biomedical signal monitoring ASIC but they also provide signal processing building blocks to shift the focus from readout front-end power optimization as discussed in the article entitled "A 200 µW Eight-Channel EEG Acquisition ASIC for Ambulatory EEG Systems" mentioned above and "A 1V 450 nW Fully Integrated Programmable Biomedical Sensor Interface System" by X D Zou, X Y Xu, L B Yao and Y Lian, IEEE J. of Solid-State Circuits, vol. 44, no. 4, pages 1067 to 1077, April 2009, which is incorporated herein by reference, towards system level power optimization and robustness. This translates into an analogue signal processor implementing not only the basic functionality of power efficient signal extraction but also proposes new circuit techniques, such as activity based sampling and low-power continuous-time (CT) electrode-tissue impedance monitoring, where the former significantly reduces the data rate and the latter improves the robustness of signal analysis against motion artefacts. The ASP 1000 in accordance with one embodiment has been implemented in a standard 0.5 μm CMOS process.

Although the present disclosure has been described with reference to the use of 64 Hz and 1024 Hz as the frequencies between which the ADC is switched, it will be appreciated that other values can also be used. Moreover, although only two frequencies are described above, this was by way of example and more than two frequencies may be used in the adaptive sampling scheme in accordance with the present disclosure.

It will be appreciated that the present disclosure is not limited to use with ECG signals and can be used for other applications where high frequency content needs to be sampled effectively when included in a lower frequency content.

The foregoing description details certain embodiments of the disclosure. It will be appreciated, however, that no matter how detailed the foregoing appears in text, the disclosure may be practiced in many ways. It should be noted that the use of particular terminology when describing certain features or aspects of the disclosure should not be taken to imply that the terminology is being re-defined herein to be restricted to including any specific characteristics of the features or aspects of the disclosure with which that terminology is associated.

While the above detailed description has shown, described, and pointed out novel features of the disclosure as applied to various embodiments, it will be understood that various omissions, substitutions, and changes in the form and details of the device or process illustrated may be made by those skilled in the technology without departing from the spirit of the disclosure. The scope of the invention is indicated by the appended claims rather than by the foregoing description. All changes which come within the meaning and range of equivalency of the claims are to be embraced within their scope.

What is claimed is:

1. A method for adaptively sampling an analogue biopotential signal, the method comprising the steps of:
   a) determining a derivative of the analogue biopotential signal;
   b) detecting a change in the derivative of the analogue biopotential signal;
   c) sampling the analogue biopotential signal using a sampling frequency; and
   d) using the change in the derivative of the analogue biopotential signal to control the sampling frequency of the analogue biopotential signal, wherein the process of controlling the sampling frequency of the analogue biopotential signal comprises comparing the change in the derivative of the analogue biopotential signal with an automatically controlled threshold value, and wherein the automatically controlled threshold value is generated from an expected average activity value and an extracted average activity value, the extracted average activity value being derived from the analogue biopotential signal, and the expected average activity value being derived from a beat frequency of the analogue biopotential signal.

2. The method according to claim 1, wherein the analogue biopotential signal comprises an electrocardiogram signal and the process d) further comprises deriving the expected average activity value from a beat frequency of the electrocardiogram signal.

3. The method according to claim 1, wherein the process c) comprises adjusting the sampling frequency to sample the analogue biopotential signal in accordance with the comparison between the derivative of the analogue biopotential signal and the threshold value.

4. The method according to claim 3, wherein the sampling frequency is increased to correspond with a high frequency component of the analogue biopotential signal.

5. The method according to claim 3, wherein the sampling frequency is decreased to correspond with other lower frequency components of the analogue biopotential signal.

6. The method according to claim 1, wherein the process c) is carried out using an analogue-to digital converter.

7. An apparatus for adaptively sampling a high frequency component of an analogue biopotential signal, the apparatus comprising:
   a sampling device configured to sample the analogue biopotential signal at a sampling frequency; and
   a control device configured to control the sampling device, the control device comprising an activity detection device configured to determine a derivative of the analogue biopotential signal and to use a change in the derivative of the analogue biopotential signal to alter the sampling frequency of the sampling device, the activity detection device comprising a comparator configured to compare the change in the derivative of the analogue biopotential signal with an automatically controlled threshold value which is generated from an expected average activity value and an extracted average activity value, the extracted average activity value being derived from the analogue biopotential signal, and the expected average activity value being derived from a beat frequency of the analogue biopotential signal.

8. The apparatus according to claim 7, wherein the comparator generates a difference between the extracted average activity value and the expected average activity value that is used to automatically control the threshold value.

9. The apparatus according to claim 8, wherein the threshold value is increased when the extracted average activity value is greater than the expected average activity value.

10. The apparatus according to claim 8, wherein the threshold value is decreased when the extracted average activity value is less than the expected average activity value.

11. The apparatus according to claim 7, wherein the activity detection device comprises a differentiator configured to generate the derivative of the analogue biopotential signal.

12. The apparatus according to claim 7, wherein the threshold value is derived from the derivative of the analogue biopotential signal.

13. The apparatus according to claim 7, wherein the sampling device comprises an analogue-to-digital converter configured to convert the analogue biopotential signal into a digital representation thereof in accordance with the sampling frequency.

14. The apparatus according to claim 7, wherein the control device comprises a digital signal processor (DSP).

15. The apparatus according to claim 14, wherein the DSP is implemented in an application specific integrated circuit.

16. A device for adaptively sampling a high frequency component of an analogue biopotential signal, the device comprising:
   means for determining a derivative of the analogue biopotential signal;
   means for detecting a change in the derivative of the analogue biopotential signal;
   means for sampling the analogue biopotential signal using a sampling frequency; and
   means for controlling the sampling frequency of the analogue biopotential signal, the means for determining further configured to use a change in the derivative of the analogue biopotential signal to alter the sampling frequency of the means for sampling, the means for determining a derivative comprising a means for comparing the change in the derivative of the analogue biopotential signal with an automatically controlled threshold value, wherein the automatically controlled threshold value is generated from an expected average activity value and an extracted average activity value, the extracted average activity value being derived from the analogue biopotential signal, and the expected average activity value being derived from a beat frequency of the analogue biopotential signal.

\* \* \* \* \*